(12) United States Patent

Takahashi et al.

(10) Patent No.: US 12,688,632 B2

(45) Date of Patent: Jul. 21, 2026

(54) SYSTEM AND METHOD FOR SYNCHRONIZED NAVIGATION AND ANNOTATION OF CORRELATED, HETEROGENEOUS SETS OF MEDICAL IMAGES

(71) Applicant: FUJIFILM Healthcare Americas Corporation, Lexington, MA (US)

(72) Inventors: Azuma Takahashi, Cary, NC (US); Myles O'Keefe, Cary, NC (US); Michael Wakim, Culver City, CA (US); Jasmine Mulligan, Seattle, WA (US); Brigil Vincent, Chapel Hill, NC (US); Takashi Hirano, Morrisville, NC (US)

(73) Assignee: FUJIFILM Healthcare Americas Corporation, Lexington, MA (US)

( * ) Notice: Subject to any disclaimer, the term of this patent is extended or adjusted under 35 U.S.C. 154(b) by 52 days.

(21) Appl. No.: 18/795,349

(22) Filed: Aug. 6, 2024

(65) Prior Publication Data

US 2026/0045007 A1 Feb. 12, 2026

(51) Int. Cl.
*G06T 11/60* (2026.01)
*G06T 7/00* (2017.01)
*G16H 30/40* (2018.01)

(52) U.S. Cl.
CPC ............ *G06T 11/60* (2013.01); *G06T 7/0012* (2013.01); *G16H 30/40* (2018.01);
(Continued)

(58) Field of Classification Search
CPC ................... G06T 11/60; G06T 7/0012; G06T 2207/10081; G06T 2207/10104;
(Continued)

(56) References Cited

U.S. PATENT DOCUMENTS 7,809,175 B2 10/2010 Roehrig et al.
8,472,684 B1 * 6/2013 Periaswamy ........... G06T 7/337
382/128

(Continued)

FOREIGN PATENT DOCUMENTS

CN 116452484 B * 9/2023 ............... G06T 5/50

OTHER PUBLICATIONS

Zhang, J., Liu, A., Wang, D., Liu, Y., Wang, Z. J., & Chen, X. (2022). Transformer-based end-to-end anatomical and functional image fusion. IEEE Transactions on Instrumentation and Measurement, 71, 1-11.*

(Continued)

*Primary Examiner* — Sarah Lhymn
(74) *Attorney, Agent, or Firm* — Woods Oviatt Gilman LLP; Dennis B. Danella, Esq.

(57) ABSTRACT

The instant disclosure relates to a method for synchronized navigation and annotation of correlated, heterogeneous sets of medical images. The method including correlating, based on first and second metadata, first and second sets of sequential tomographic medical images of a subject and thereby generate correlated image pairs. Superimposing each correlated image pair to generate fusion images corresponding to the correlated image pairs. Selectively and sequentially rendering the correlated image pairs, the fusion images, and/or a third tomographic medical (TTM) image of the subject. Selectively rendering a visual representation of a pixel of interest and/or region of interest for the correlated image pairs, the fusion images, and/or the TTM image. A machine learning algorithm is used to identify a pixel within a medical image that is associated with a medical condition. A graphical annotation is rendered on or about the pixel's location.

20 Claims, 5 Drawing Sheets

(52) U.S. Cl.
CPC ............... *G06T 2207/10081* (2013.01); *G06T 2207/10104* (2013.01); *G06T 2207/20081* (2013.01); *G06T 2207/30004* (2013.01); *G06T 2210/41* (2013.01)

(58) Field of Classification Search
CPC . G06T 2207/20081; G06T 2207/30004; G06T 2210/41; G16H 30/40
See application file for complete search history.

(56) References Cited

U.S. PATENT DOCUMENTS

| | | | |
|---|---|---|---|
| 9,183,355 B2 | 11/2015 | Gustafson | |
| 10,307,124 B2 * | 6/2019 | Li | G06T 7/55 |
| 10,520,568 B2 | 12/2019 | Moskal | |
| 10,956,635 B1 | 3/2021 | Douglas et al. | |
| 11,210,785 B1 | 12/2021 | Douglas et al. | |
| 11,263,749 B1 * | 3/2022 | Purushottam | G06T 7/0012 |
| 11,672,614 B1 * | 6/2023 | Roh | A61B 5/0035 |
| | | | 382/153 |
| 2003/0007598 A1 | 1/2003 | Wang et al. | |
| 2007/0211930 A1 | 9/2007 | Dolwick et al. | |
| 2008/0043036 A1 | 2/2008 | Evertsz et al. | |
| 2021/0035296 A1 * | 2/2021 | Mahrooghy | G06F 18/24323 |
| 2021/0210196 A1 * | 7/2021 | Ye | G16H 30/40 |
| 2022/0336071 A1 | 10/2022 | Laugerette et al. | |
| 2023/0197253 A1 * | 6/2023 | Nakamura | A61B 6/00 |
| | | | 382/128 |
| 2023/0351586 A1 | 11/2023 | Brynolfsson et al. | |
| 2023/0355195 A1 | 11/2023 | Averbuch | |
| 2023/0410985 A1 * | 12/2023 | Brynolfsson | G06T 7/30 |
| 2024/0127437 A1 | 4/2024 | Anand et al. | |
| 2024/0285248 A1 * | 8/2024 | Sjöstrand | G16H 50/30 |

OTHER PUBLICATIONS

Kumar, A., Fulham, M., Feng, D., & Kim, J. (2019). Co-learning feature fusion maps from PET-CT images of lung cancer. IEEE Transactions on Medical Imaging, 39(1), 204-217.*

Gabarre, S., Vernaillen, F., Baatsen, P., Vints, K., Cawthorne, C., Boeynaems, S., . . . & Munck, S. (2021). A workflow for streamlined acquisition and correlation of serial regions of interest in array tomography. BMC biology, 19(1), 152.*

Quick, Harald H., "Whole-Body MR/PET Hybrid Imaging: Technical Considerations, Clinical Workflow, and Initial Results", MAGNETOM Flash, (2011), pp. 88-100.

Im, Ki Chun, "PET/CT Fusion Viewing Software for Use with Picture Archiving and Communication Systems", Journal of Digital Imaging, vol. 23, No. 6, (2010), pp. 732-743.

Bankwitz, Robert, "Extended European Search Report", European Patent Application No. 251607529 filed on Feb. 27, 2025, mailed on Aug. 18, 2025, Munich, Germany.

Jones, Terry, "Total Body PET Imaging From Mice to Humans", Frontiers in Physics, vol. 8, Article 77, (2020), pp. 1-4.

* cited by examiner

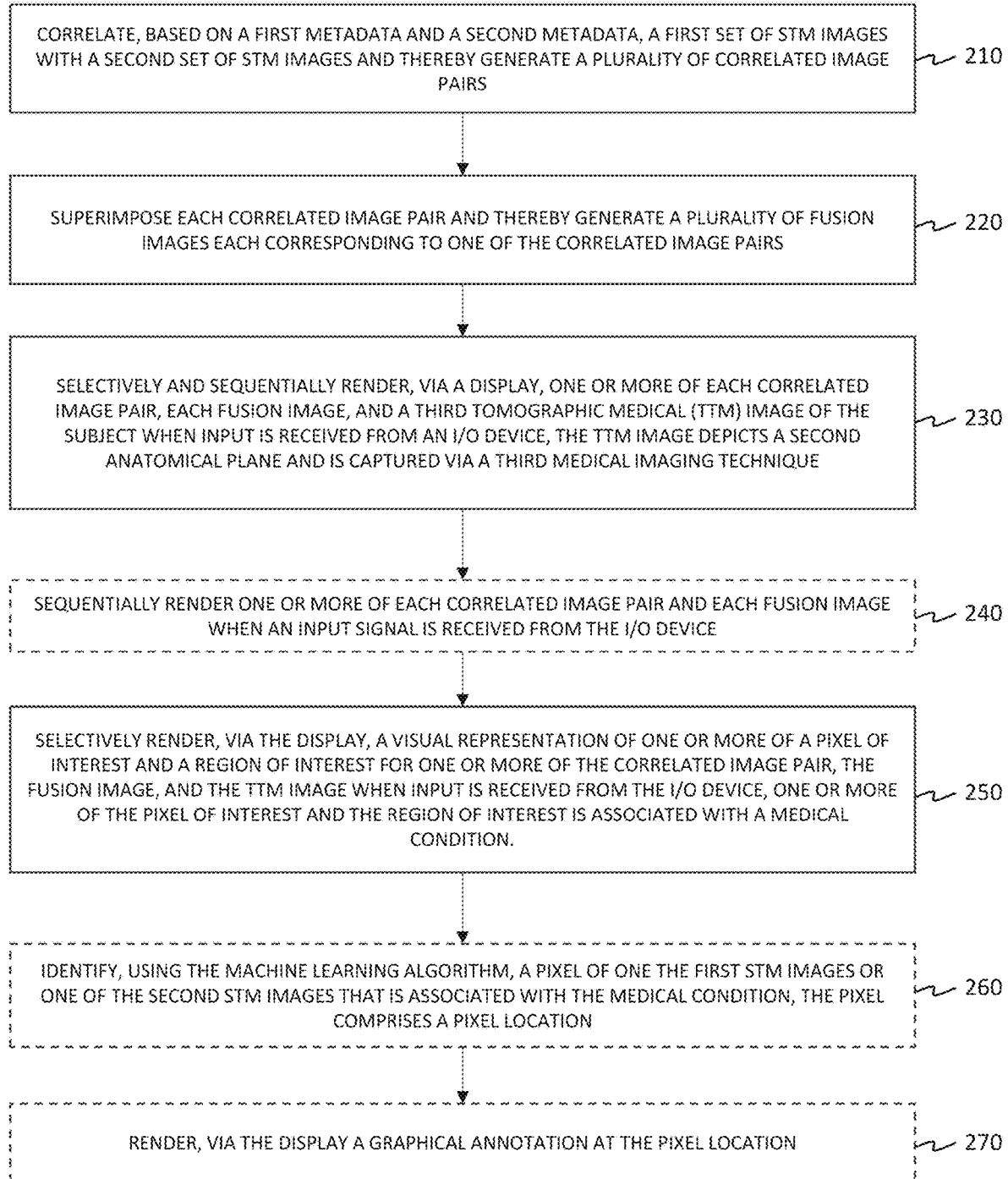

CORRELATE, BASED ON A FIRST METADATA AND A SECOND METADATA, A FIRST SET OF STM IMAGES WITH A SECOND SET OF STM IMAGES AND THEREBY GENERATE A PLURALITY OF CORRELATED IMAGE PAIRS — 210

SUPERIMPOSE EACH CORRELATED IMAGE PAIR AND THEREBY GENERATE A PLURALITY OF FUSION IMAGES EACH CORRESPONDING TO ONE OF THE CORRELATED IMAGE PAIRS — 220

SELECTIVELY AND SEQUENTIALLY RENDER, VIA A DISPLAY, ONE OR MORE OF EACH CORRELATED IMAGE PAIR, EACH FUSION IMAGE, AND A THIRD TOMOGRAPHIC MEDICAL (TTM) IMAGE OF THE SUBJECT WHEN INPUT IS RECEIVED FROM AN I/O DEVICE, THE TTM IMAGE DEPICTS A SECOND ANATOMICAL PLANE AND IS CAPTURED VIA A THIRD MEDICAL IMAGING TECHNIQUE — 230

SEQUENTIALLY RENDER ONE OR MORE OF EACH CORRELATED IMAGE PAIR AND EACH FUSION IMAGE WHEN AN INPUT SIGNAL IS RECEIVED FROM THE I/O DEVICE — 240

SELECTIVELY RENDER, VIA THE DISPLAY, A VISUAL REPRESENTATION OF ONE OR MORE OF A PIXEL OF INTEREST AND A REGION OF INTEREST FOR ONE OR MORE OF THE CORRELATED IMAGE PAIR, THE FUSION IMAGE, AND THE TTM IMAGE WHEN INPUT IS RECEIVED FROM THE I/O DEVICE, ONE OR MORE OF THE PIXEL OF INTEREST AND THE REGION OF INTEREST IS ASSOCIATED WITH A MEDICAL CONDITION. — 250

IDENTIFY, USING THE MACHINE LEARNING ALGORITHM, A PIXEL OF ONE THE FIRST STM IMAGES OR ONE OF THE SECOND STM IMAGES THAT IS ASSOCIATED WITH THE MEDICAL CONDITION, THE PIXEL COMPRISES A PIXEL LOCATION — 260

RENDER, VIA THE DISPLAY A GRAPHICAL ANNOTATION AT THE PIXEL LOCATION — 270

FIG. 2

SYSTEM AND METHOD FOR SYNCHRONIZED NAVIGATION AND ANNOTATION OF CORRELATED, HETEROGENEOUS SETS OF MEDICAL IMAGES

TECHNICAL FIELD

The present invention relates to the field of medical imaging; and more particularly relates to a system and method for synchronized navigation and annotation of correlated, heterogeneous sets of medical images.

BACKGROUND OF THE INVENTION

Medical imaging is the technique and process of capturing images of the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging also establishes a database of normal anatomy and physiology to make it possible to identify abnormalities. Imaging of removed organs and tissues can also be performed for medical reasons. Medical diagnosis can be performed using medical images obtained by imaging apparatuses such as computed tomography (CT) imaging apparatuses, positron emission tomography (PET) imaging apparatuses, and magnetic resonance imaging (MRI) imaging apparatuses. Whole-Body Maximum Intensity Projection (MIP) imaging can also be used for medical diagnosis.

However, the amount of information from the medical images and the Computer Aided Detection (CAD) based analysis presented to the healthcare professional has increased with performance increase of the imaging apparatus and CAD-based analysis. When a plethora of images are obtained and analyzed, navigating and annotating the results and images can complicate the confirmation work for healthcare professionals.

Accordingly, there exists a need for improved methods and apparatuses for navigating and annotating correlated, heterogeneous sets of medical images. The present invention addresses this need as well as other needs.

SUMMARY OF THE INVENTION

It is, therefore, an aspect of the present invention to provide a computer system for synchronized navigation and annotation of correlated, heterogeneous sets of medical images, the system includes: a computer processor; a computer-readable storage media, and program instructions stored on the computer-readable storage media for execution by the processor, the program instructions include program instructions to correlate, based on a first metadata and a second metadata, a first set of sequential tomographic medical (STM) images of a subject with a second set of STM images of the subject and thereby generate a plurality of correlated image pairs.

The first set of STM images each include the first metadata, depict a first anatomical plane, and are captured via a first medical imaging technique (MIT). The second set of STM images each include the second metadata, depict the first anatomical plane, and are captured via a second MIT. The program instructions further include program instructions to superimpose each correlated image pair and thereby generate a plurality of fusion images each corresponding to one of the correlated image pairs; selectively and sequentially render, via a display, one or more of the correlated image pairs, the fusion images, and a third tomographic medical (TTM) image of the subject when input is received from an I/O device, the TTM image depicts a second anatomical plane and is captured via a third MIT; and selectively render, via the display, a visual representation of one or more of a pixel of interest and a region of interest for one or more of the correlated image pairs, the fusion images, and the TTM image when input is received from the I/O device.

The program instructions can further include program instructions to identify, using a machine learning algorithm, a pixel of one the first STM images or one of the second STM images that is associated with the medical condition and render, via the display a graphical annotation at the pixel location of the pixel. The machine learning algorithm is trained with predetermined medical images that each depict either a presence of the medical condition or absence of the medical condition within an anatomical region of the predetermined medical images. The presence of the medical condition is dictated by a pixel value within the anatomical region that is greater than or less than a predetermined value. The program instructions can further include program instructions to render, via the display, a second graphical annotation that encompasses the pixel location and thereby selectively render the visual representation of the region of interest.

Another aspect of the present invention provides computer-implemented method for synchronized navigation and annotation of correlated, heterogeneous sets of medical images. The method correlates, using first metadata and second metadata, a first set of sequential tomographic medical (STM) images of a subject with a second set of STM images of the subject and thereby generates a plurality of correlated image pairs. The first set of STM images include the first metadata, each depict a first anatomical plane, and are captured via a first medical imaging technique (MIT). The second set of STM images include the second metadata, each depict the first anatomical plane, and are captured via a second MIT. Each correlated image pair is superimposed and thereby generates a plurality of fusion images each corresponding to one of the correlated image pairs.

One or more of each correlated image pair, each fusion image, a third tomographic medical (TTM) image of the subject when input is received from an I/O device. The TTM image depicts a second anatomical plane and is captured via a third MIT. A visual representation of one or more of a pixel of interest and a region of interest for one or more of the correlated image pair, the fusion image, and the coronal plane image is selectively rendered, via the display, when input is received from the I/O device. One or more of the pixel of interest and the region of interest is associated with a medical condition.

Certain aspects of the present invention provide a computer program product that includes a computer readable storage medium having program code embodied therewith that is executable by a processor to correlate, based on a first metadata and a second metadata, a first set of sequential tomographic medical (STM) images of a subject with a second set of STM images of the subject and thereby generate a plurality of correlated image pairs. The first set of STM images each include the first metadata, depict a first anatomical plane, and are captured via a first medical imaging technique (MIT). The second set of STM images each include the second metadata, depict the first anatomical plane, and are captured via a second MIT. The processor executes program code to superimpose each correlated image pair and thereby generate a plurality of fusion images that each correspond to one of the correlated image pairs.

The processor executes program code to selectively and sequentially render, via a display, one or more of the correlated image pairs, the fusion images, and a third tomographic medical (TTM) image of the subject when input is received from an I/O device. The TTM image depicts a second anatomical plane and is captured via a third MIT. The processor executes program code to selectively render, via the display, a visual representation of one or more of a pixel of interest and a region of interest for one or more of the correlated image pairs, the fusion images, and the TTM image when input is received from the I/O device. One or more of the pixel of interest and the region of interest is associated with a medical condition.

Additional aspects, advantages and novel features of the present invention will be set forth in part in the description which follows and will in part become apparent to those in the practice of the invention, when considered with the attached figures.

BRIEF DESCRIPTION OF THE DRAWINGS

The present invention will now be described, by way of example, with reference to the accompanying drawings, in which:

FIG. 2 is a flow chart depicting operational steps of an information processing program, on a computing device within the information processing environment of FIG. 1, for synchronizing, navigating, and annotating correlated, heterogeneous sets of medical images, in accordance with certain embodiments;

Corresponding reference characters indicate corresponding parts throughout the several views. The exemplifications set out herein illustrate currently preferred embodiments of the invention, and such exemplifications are not to be construed as limiting the scope of the invention in any manner.

DETAILED DESCRIPTION

Figure 1A:
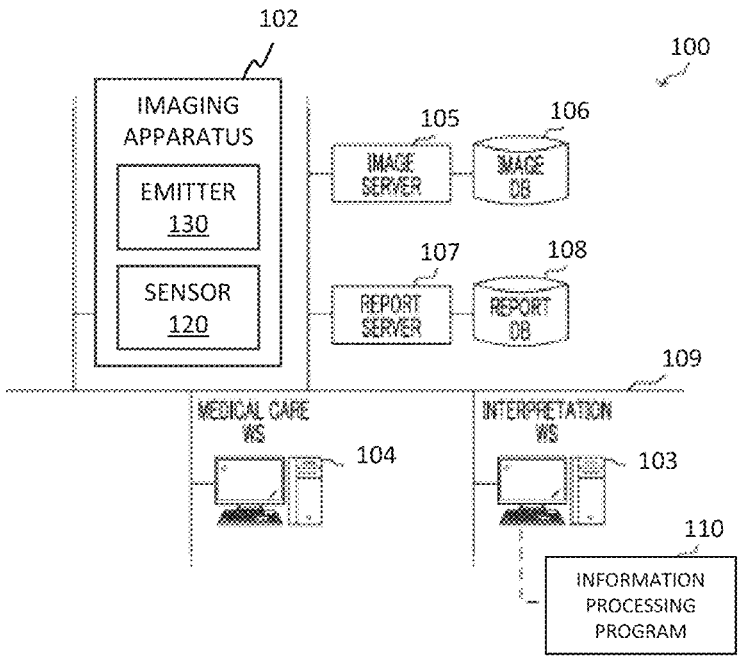
FIG. 1A is a block diagram illustrating an information processing environment, for synchronizing, navigating, and annotating correlated, heterogeneous sets of medical images, in accordance with some embodiments.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer-readable medium(s) having computer-readable program code/instructions embodied thereon.

Any combination of computer-readable media may be utilized. Computer-readable media may be a computer-readable signal medium or a computer-readable storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of a computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain, or store a program for use by or in connection with an instruction execution system, apparatus, or device.

Program code embodied on a computer-readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object-oriented programming language such as Java, Smalltalk, C++ or the like and conventional procedural programming languages, such as the "C" programming language or similar programming languages. The program code may execute entirely on a user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer, other programmable data processing apparatus, or other devices to function in a particular manner, such that the instructions stored in the computer-readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer-implemented process such that the instructions which execute on the computer or other programmable apparatus provide processes for implementing the functions/acts specified in the flowchart and/or block diagram block or blocks.

Medical imaging is the technique and process of capturing images of the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging also establishes a database of normal anatomy and physiology to make it possible to identify abnormalities. Imaging of removed organs and tissues can also be performed for medical reasons. Medical diagnosis can be performed using medical images obtained by imaging apparatuses such as computed tomography (CT) imaging apparatuses, positron emission tomography (PET) imaging apparatuses, and magnetic resonance imaging (MRI) imaging apparatuses. Whole-Body Maximum Intensity Projection (MIP) imaging can also be used medical diagnosis.

However, the amount of information derived from the medical images and Computer Aided Detection (CAD) based analysis presented to the healthcare professional has increased with the performance increase of the imaging apparatus and CAD-based analysis. When a plethora of images are obtained and analyzed, navigating and annotating the results and images can complicate the confirmation work for healthcare professionals. Accordingly, there exists a need for improved methods and apparatuses for navigating and annotating correlated, heterogeneous sets of medical images. The present invention addresses this need as well as other needs.

With initial reference to FIG. 1, a block diagram illustrating an information processing environment, generally 100, for capturing, storing, and/or analyzing medical images, in accordance with an embodiment of the present invention is provided. The information processing environment can include one or more of an imaging apparatus 102, one or more servers (e.g., an image server 105 and a report server 107), and computing devices (e.g., a medical care workstation (WS) 104 and an interpretation WS 103) communicatively coupled together via a network 109. Two or more of the aforementioned components may be combined in a single unit. The network 109 can be made up of telecommunication network technologies that are based on physically wired, optical, and/or wireless radio-frequency methods that may be arranged in a variety of network topologies. In general, the network 109 can be any set of digital interconnections that allow computing devices to use common communication protocols to communicate with each other.

Imaging apparatus 102 may be one or more imaging devices that include an emitter 130 and a sensor 120. Imaging apparatus 102 is configured to scan the body of a subject by exposing the subject to signals emitted by emitter 130, capturing those signals (or signal reflections) via sensor 120, and thereby obtain detailed internal images of the subject's body (e.g., images of the anatomy and the physiological processes inside the body). The medical images generated by imaging apparatus 102 may be stored in image database 106 and/or other database that is communicatively coupled to network 109. For example, imaging apparatus 102 is configured to generate sequential tomographic images of a subject. Imaging apparatus 102 may capture tomographic images along one or more anatomical planes (e.g., the transaxial plane, coronal plane, sagital plane, median plane, parasagittal plane, and other anatomical planes) of subjects.

Figure 1B:
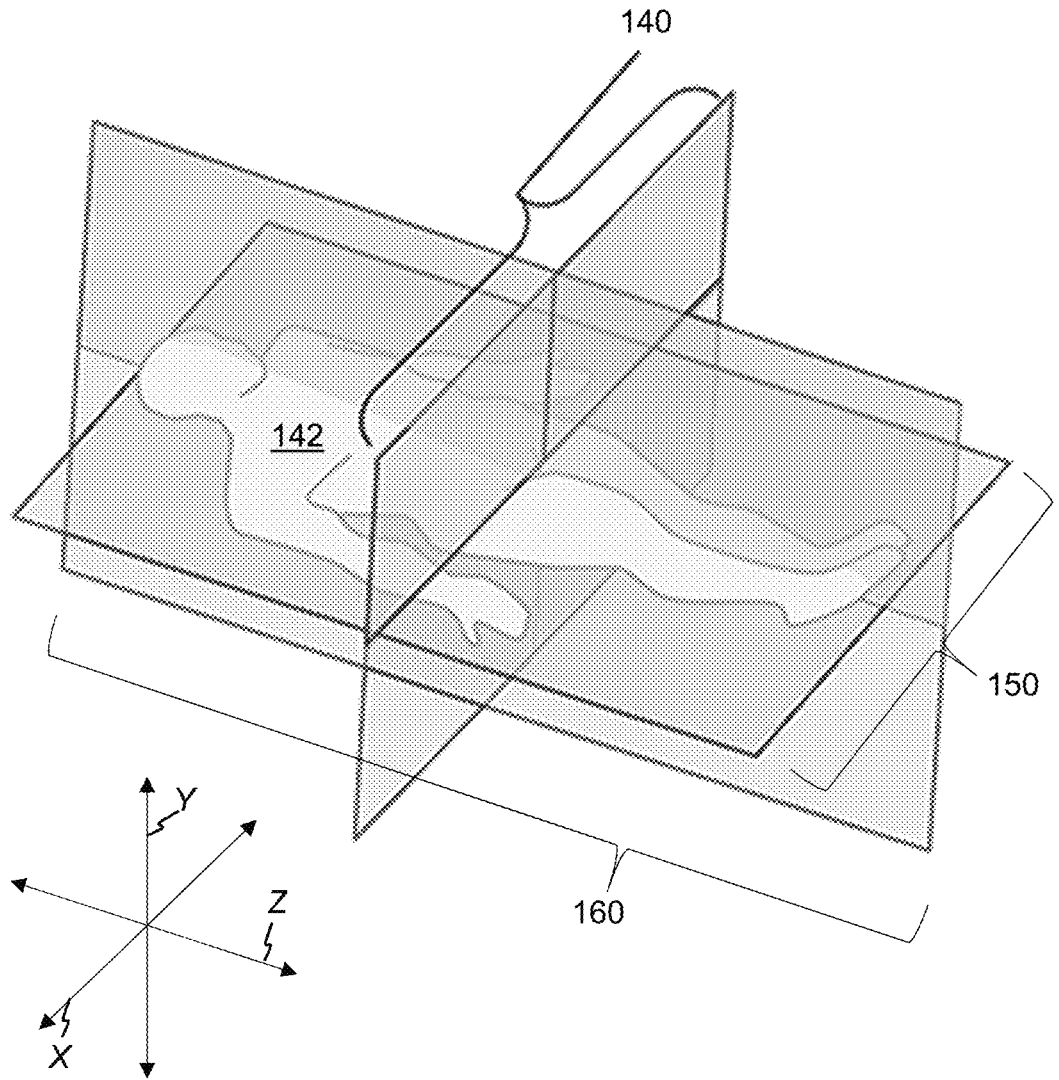
FIG. 1B is an illustration that depicts the transaxial plane, coronal plane, and sagittal plane of a subject, in accordance with other embodiments.

Turning now to FIG. 1B, for example, each subject 142 (e.g., a human, mammal, other biological entity, or portion thereof) has a primary body axis, or z-axis, extending from the pelvis through the center of the body to the top of the head. A transaxial plane 140, otherwise known as the axial or transverse plane, is located perpendicular to the z-axis in the x-y plane, and can be taken anywhere along the z-axis. A coronal, or frontal, plane 150 extends in the left-right direction in the x-z plane, and can be taken anywhere along the y-axis. A sagittal plane 160 extends in the anterior-posterior direction in the y-z plane, and can be taken anywhere along the x-axis. When sagittal plane 160 bisects the body into left and right halves it is commonly referred to as the midsagittal plane. The x-axis and y-axis lie in the transaxial plane. Although medical image display systems permit the operator to view any anatomical plane, the transaxial, coronal, and sagittal planes are routinely used in medical imaging to visualize anatomy and describing findings.

Applicable signals emitted by emitter 130 include, but are not limited to, strong magnetic fields, magnetic field gradients, radio waves, X-rays, and ionizing radiation. Imaging apparatus 102 preferably generates heterogeneous sequential tomographic images of the subject. Imaging apparatus 102 can generate medical images using one or more medical imaging techniques that include, but are not limited to, X-ray, computed tomography (CT) scan, magnetic resonance imaging (MRI), positron emission tomography (PET), maximum intensity projection (MIP), and/or other medical imaging technique capable of generating internal images of a subject's body or part thereof.

The servers may each include a software program providing a database management system (DBMS) installed therein. In some embodiments, image server 105 and report server 107 can be included in one or more computing devices. The servers may include one or more storage media (e.g., flash memory, solid state drive (SSD), or hard disk drive (HDD)) for storing information. For example, image server 105 can include an image database (DB) 106 for at least storing medical images. Report server 107 may include a report DB 108 for at least storing processed reports. Medical care WS 104 can be used by healthcare professionals (e.g., doctors and nurses) to at least observe medical images in detail, view interpretation reports, and/or generate electronic medical records.

Medical care WS 104 may transmit a viewing request for medical images to image server 105, display the received medical images, transmit a viewing request for the associated interpretation report(s) to report server 107, and/or display the received interpretation report. Medical care WS 104 may perform the above processes via executing software programs for respective processes. The steps described in the instant disclosure may be performed by one or more control circuits and/or processors. The interpretation reports can include images analyzed by an information processing program 110 included in interpretation WS 103 (or other computing device communicatively coupled to network 109).

Interpretation WS 103 is a computing device that can be configured to analyze or interpret one or more medical images (e.g., stored in image DB 106 or other datastore communicatively coupled to network 109) as described in the present disclosure. Interpretation WS 103 may be used by user (e.g., a healthcare professional) to interpret one or more medical images and/or create interpretation reports. Interpretation WS 103, or other processor(s) communicatively coupled to network 109, can perform steps defined by an information processing program 110. As will be discussed in more detail below, information processing program 110 is computer code that enables the synchronized navigation and annotation of correlated, heterogeneous sets of medical images. Information processing program 110 can be stored in a database communicatively coupled to the interpretation WS 103. Alternatively, information processing program 110 can be stored in one or more databases that are communicatively coupled to network 109.

As seen in FIG. 2, a flow chart is provided and depicts operational steps of information processing program 110, on a computing device within the information processing environment of FIG. 1, for synchronizing, navigating, and annotating correlated, heterogeneous sets of medical images, in accordance with aspects of the present invention. At Step 210, a first set of STM images is correlated with a second set of STM images, based on first metadata and second metadata, and thereby generates a plurality of correlated image pairs. Applicable metadata may include, but is not limited to, identification information such as an image identification (ID) for identifying a medical image, Digital Imaging and Communications in Medicine (DICOM) information, a tomographic ID assigned to each tomographic image included in the medical images, a subject ID for identifying a subject, and an examination ID for identifying an examination.

Further, applicable metadata may include, but is not limited to, imaging information related to imaging method, imaging conditions, imaging sequence information, anatomical viewing information, and image capture date/time. Tomographic medical images of the instant disclosure provide can be digitally "stacked" together to provide users a sequential view of the subject's body or portion thereof along an anatomical plane. The metadata is used to correlate sets of medical images of the subject according to their sequential position regardless of the anatomical position the medical images are captured in.

The first set of STM images each include the first metadata, depict a first anatomical plane, and are captured via a first medical imaging technique (MIT). The second set of STM images each include the second metadata, depict the first anatomical plane, and are captured via a second MIT.

For example, the first set of STM images and the second set of STM images are retrieved from image database 106. With additional reference to FIG. 3, the first set of STM images may be transaxial images generated via CT scan and include image 306. CT scan images readily identify anatomical structures such as the pelvis, ribs, spine, liver, esophagus, sub-cutaneous adipose tissue, etc. The second set of STM images may be transaxial images generated via PET and include image 311. PET scan images readily identify measured changes in metabolic processes, and in other physiological activities including blood flow, regional chemical composition, and absorption (e.g., to identify tumors, metastases, brain pathologies, vascular disease/ailments, etc.). The first metadata and the second metadata are used to positionally correlate each transaxial CT image of the first set of STM images with a transaxial PET image of the second STM images.

At Step 220, each correlated image pair (e.g., image 306 and image 311) is superimposed together and thereby generates a plurality of fusion images that each correspond to one of the correlated image pairs. For example, fusion image

Figure 3:
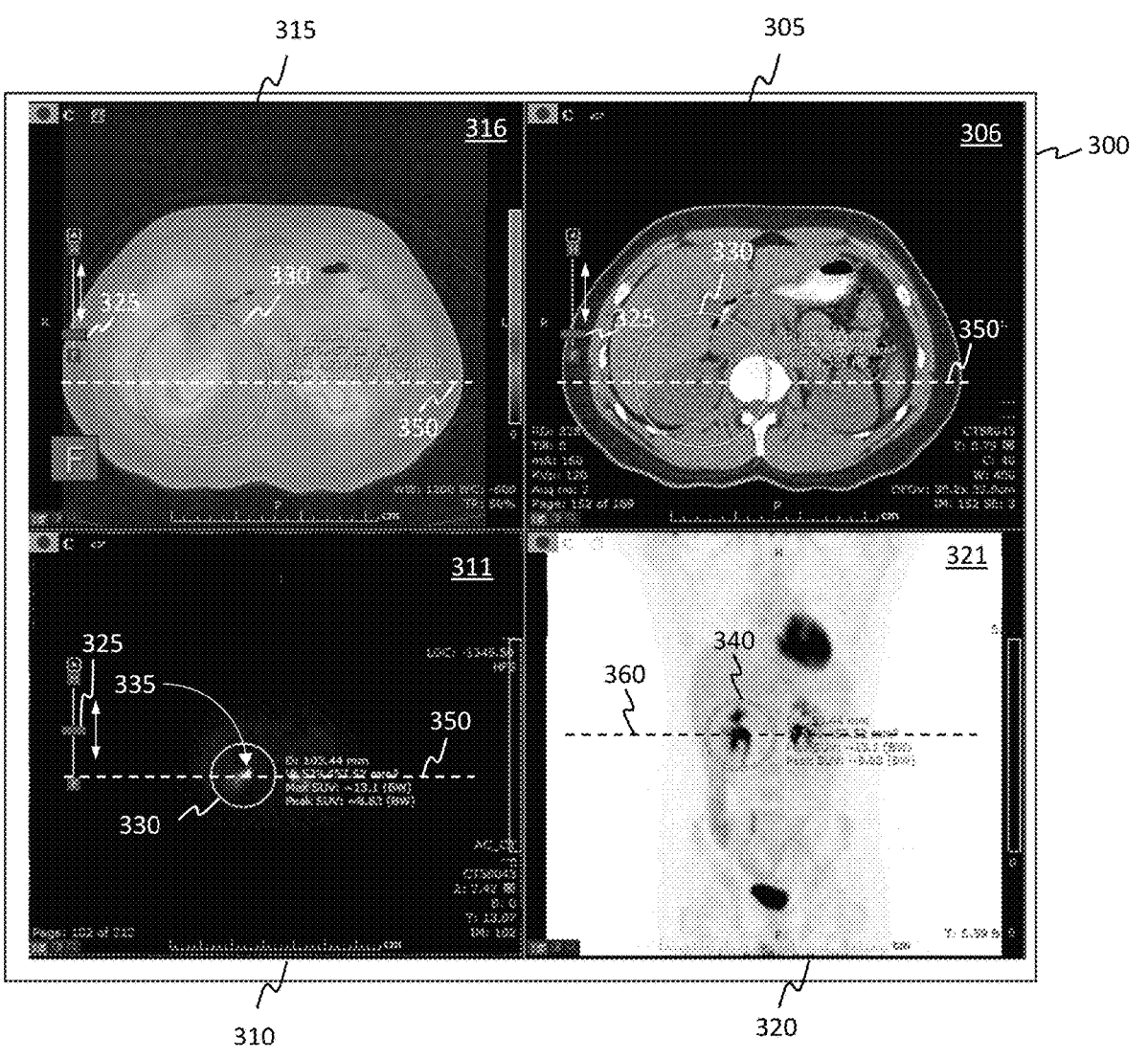
FIG. 3 illustrates a graphical user interface (GUI), that renders medical images within the information processing environment of FIG. 1, in accordance with yet still other embodiments.

316 correlates to an image pair that consists of image 306 superimposed with image 311. FIG. 3 illustrates a graphical user interface (GUI), generally 300, that renders medical images within the information processing environment of FIG. 1, in accordance with other embodiments. GUI 300 is rendered in a display (e.g., display 620) and can include one or more viewing panes (hereinafter "panes") that the medical images are rendered in. GUI 300 may include, but is not limited to, a pane 305, a pane 310, a pane 315, and a pane 320.

At Step 230, one or more of each correlated image pair, each fusion image, and a third tomographic medical (TTM) image (e.g., image 321) of the subject are selectively rendered, via a display (e.g., display 620), when input is received from an I/O device (see external components 600 below), the TTM image depicts a second anatomical plane and is captured via a third medical imaging technique. Image 321 is a MIP image that depicts the coronal view of the subject. As shown, the correlated image pair of image 306 and image 311 are rendered within pane 305 and pane 310, respectively. Fusion image 316 of image 306 and image 311 is rendered within pane 315. Image 321 is rendered within pane 320. Hence, the user can use GUI 300 to view the results of three different medical imaging techniques captured via two different anatomical planes.

In other embodiments, GUI 300 includes an annotation icon 350 (depicted in pane 305, pane 310, and pane 315) and/or an annotation icon 360. Annotation icon 350 represents the anatomical position of image 321 relative to fusion image 316, image 306, and image 311. Annotation icon 360 represents the anatomical position of fusion image 316, image 306, and/or image 311 relative to image 321. Users can positionally manipulate, via one or more of external components 600, the annotation icon 350 to sequentially change the TTM image depicted in pane 320. Alternatively, users can positionally manipulate, via one or more of external components 600, the annotation icon 360 up or down to sequentially change the fusion image, the first STM image, and/or the second STM image depicted in pane 315, pane 305, and pane 310, respectively.

At Step 240, to implement Step 230, one or more of each correlated image pair and each fusion image are sequentially rendered when an input signal is received from the I/O device. For example, one or more panes of GUI 300 can include a GUI element 325 that allows a user to selectively and sequentially view the medical images that are rendered within one or more of the panes. In other words, users can manipulate GUI element 325 to visually traverse along the anatomical plane that the medical images are captured along. At Step 250, a visual representation of one or more of a pixel of interest (e.g., pixel of interest 335) and a region of interest (e.g., region of interest 330) for one or more of the correlated image pair, the fusion image, and the TTM image are selectively rendered, via the display, when input is received from the I/O device. The pixel of interest and region of interest represent areas of the image (i.e., pixel locations) that possibly depict a medical condition. Pixels each have a pixel location. A region of interest typically has one or more of a length, width, and/or height as measured in pixels.

In certain embodiments, Step 250 is accomplished using a machine learning algorithm. A machine learning algorithm is a type of mathematical model that, after being "trained" on a given dataset (e.g., predefined medical images that depict the presence or absence of the aforementioned medical condition) to make predictions or classifications on new data (e.g., medical images). During training, a learning algorithm iteratively adjusts the model's internal parameters to minimize errors in its predictions. In preferred embodiments, a machine learning algorithm is trained with predefined medical images that each depict the presence of a medical condition or absence of the medical condition within an anatomical region of the medical image. The presence of the medical condition can be dictated by a pixel value within the anatomical region that is greater than or less than a predetermined value (or value range). In other words, image pixels having a pixel value greater than or less than the predetermined value (or value range), referred to as the pixel of interest, are identified by the machine learning algorithm as being associated with a medical condition that the machine learning algorithm is trained to detect.

When Step 250 is implemented to render a visual representation (e.g., an annotation icon or pixel color change) of the pixel of interest, at Step 260, a pixel of one the first STM images or one of the second STM images that is associated with the medical condition is identified using the machine learning algorithm. The pixel has a pixel location in its associated medical image. GUI 300 renders a graphical annotation at (or proximate to) the pixel location. If no pixel is identified, GUI 300 can render a notification to the user that conveys the absence of the pixel. In the instant example, the machine learning algorithm identified a pixel of interest and GUI 300 rendered a graphical annotation 335 at (or proximate to) the corresponding pixel location in image 311. When Step 250 is implemented to render a visual representation of the region of interest, at Step 260, a second graphical annotation that encompasses (or is positioned proximate to) the pixel location is rendered. Here, once the pixel is identified, GUI 300 rendered graphical annotation 330 that encompasses graphical annotation 335 positioned at the pixel location. Applicable graphical annotations include, but are not limited to, any graphical color, geometric shape, and/or icon that can be used to visually identify a pixel, pixel location, pixel of interest, and/or region of interest.

Since image 311 is correlated with image 306, GUI 300 further renders annotation icon 350 on image 306 and fusion image 316 in their respective viewing panes. Users can positionally manipulate annotation icon 350 within pane 305, pane 310, and/or pane 315 to sequentially traverse the TTM images rendered in the pane 320 to thereby explore the region of interest as captured in the second anatomical plane. Alternatively, users can positionally manipulate annotation icon 360 within pane 320 to sequentially traverse the medical images rendered in pane 305, pane 310, and/or pane 315 to thereby explore the region of interest as captured in the first anatomical plane.

Figure 4:
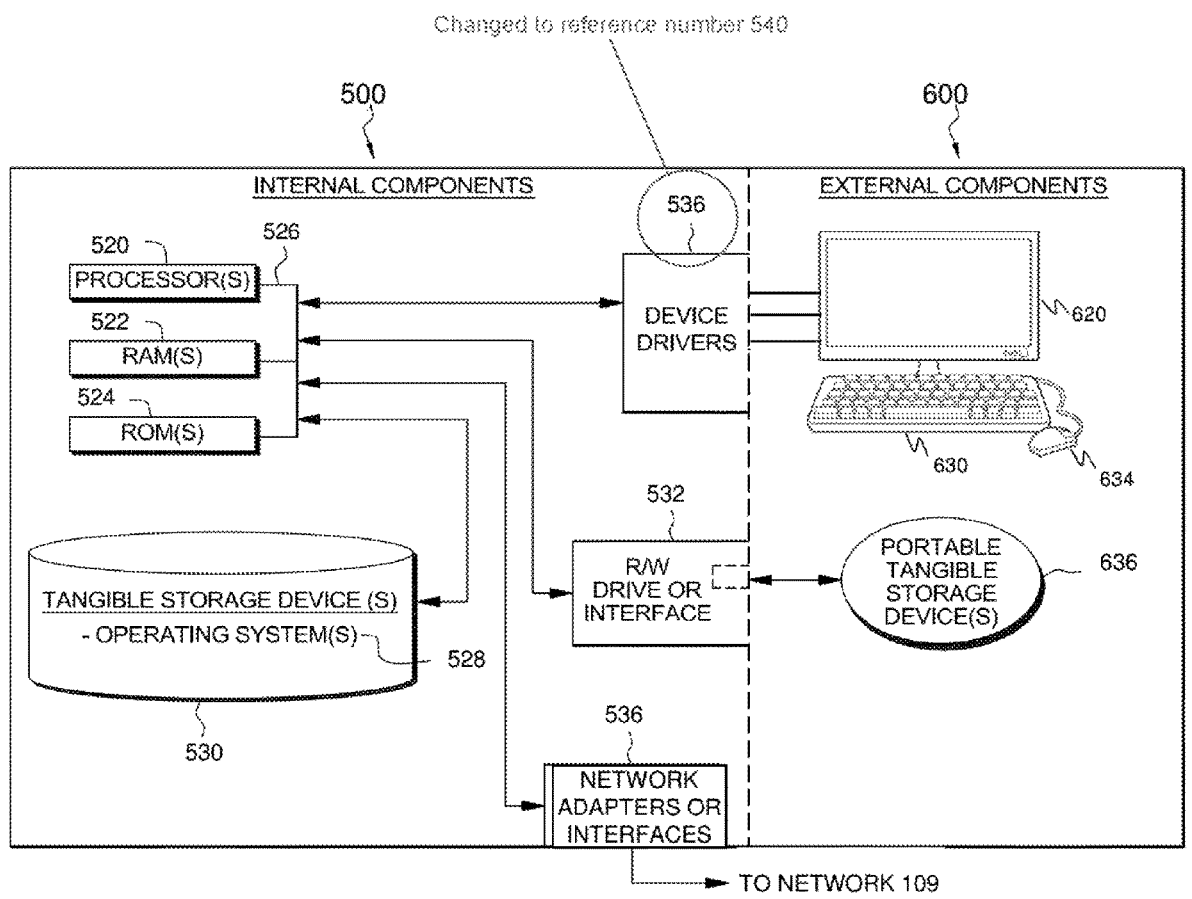
FIG. 4 depicts a block diagram of components of the computing devices executing the information processing program, in accordance with some embodiments.

FIG. 4 depicts a block diagram of components of interpretation WS 103, medical care WS 104, and/or imaging apparatus 102, in accordance with an embodiment of the present invention. Data processing system 500, 600 is representative of any electronic device capable of executing machine-readable program instructions. Data processing system 500, 600 may be representative of a smart phone, a computer system, PDA, or other electronic devices. Examples of computing systems, environments, and/or configurations that may represented by data processing system 500, 600 include, but are not limited to, personal computer systems, server computer systems, thin clients, thick clients, wearable computer, hand-held or laptop devices, multiprocessor systems, microprocessor-based systems, network PCs, minicomputer systems, and distributed cloud computing environments that include any of the above systems or devices.

Interpretation WS 103, medical care WS 104, and/or imaging apparatus 102 include respective sets of internal components 500 and external components 600 as illustrated in FIG. 4. Each of the sets of internal components 500 may include one or more processors 520, one or more computer-readable RAMs 522 and one or more computer-readable ROMs 524 on one or more buses 526, and one or more operating systems 528 and one or more computer-readable tangible storage devices 530. The information processing program 110 is stored on one or more of the respective computer-readable tangible storage devices 530 for execution by one or more of processors 520 via one or more of the respective RAMs 522 (which typically include cache memory). In the embodiment illustrated in FIG. 4, each of computer-readable tangible storage devices 530 may be a magnetic disk storage device of an internal hard drive. Alternatively, each of the computer-readable tangible storage devices 530 may be a semiconductor storage device, such as ROM 524, EPROM, flash memory or any other computer-readable tangible storage device that can store a computer program and digital information.

Internal components 500 also include a R/W drive or interface 532 to read from and write to one or more portable computer-readable tangible storage devices 636, such as a CD-ROM, DVD, memory stick, magnetic tape, magnetic disk, optical disk or semiconductor storage device. Information processing program 110 can be stored on one or more of the respective portable computer-readable tangible storage devices 636, read via the respective R/W drive or interface 532 and loaded into the respective computer-readable tangible storage devices 530.

Each set of internal components 500 also includes network adapters or interfaces 536 such as a TCP/IP adapter cards, wireless Wi-Fi interface cards, or 3G or 4G wireless interface cards or other wired or wireless communication links. The information processing program 110 can be downloaded to interpretation WS 103, medical care WS 104, and/or imaging apparatus 102, from an external computer via a network (for example, the Internet, a local area network or other, wide area network) and respective network adapters or interfaces 536. From the network adapters or interfaces 536, information processing program 110 may be loaded into the respective computer-readable tangible storage devices 530. The network may comprise copper wires, optical fibers, wireless transmission, routers, firewalls, switches, gateway computers and/or edge servers.

Each of the sets of external components 600 can include a computer display monitor 620, a keyboard 630, and a computer mouse 634. External components 600 can also include touch screens, virtual keyboards, touch pads, pointing devices, and other human interface devices. Internal components 500 also include device drivers 540 to interface to computer display monitor 620, keyboard 630 and computer mouse 634. The device drivers 540, R/W drive or interface 532 and network adapters or interfaces 536 comprise hardware and software (stored in storage device 530 and/or ROM 524).

Computer program code for carrying out operations of the present invention may be written in any combination of one or more programming languages, including an object-oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network ("LAN") or a wide area network ("WAN"), or the connection may be made to an external computer (for example, though the Internet using an Internet Service Provider).

Based on the foregoing, computer system, method and program product have been disclosed in accordance with the present invention. However, numerous modifications and substitutions can be made without deviating from the scope of the present invention. Therefore, the present invention has been disclosed by way of example and not limitation.

What is claimed is:

1. A computer system for synchronized navigation and annotation of correlated, heterogeneous sets of medical images, the system comprising:
- one or more computer processors;
- one or more computer-readable storage media;
- program instructions stored on the computer-readable storage media for execution by at least one of the one or more processors, the program instructions comprising:
- program instructions to:
  - correlate, based on a first metadata and a second metadata, a first set of sequential tomographic medical (STM) images of a subject with a second set of STM images of the subject to generate a plurality of correlated image pairs,
    - wherein the first set of STM images each comprise the first metadata, depict a first anatomical plane, and are captured via a first medical imaging technique (MIT),
    - wherein the second set of STM images each comprise the second metadata, depict the first anatomical plane, and are captured via a second MIT;
  - superimpose each of the plurality of correlated image pairs to generate a plurality of fusion images each corresponding to one of the correlated image pairs;
  - selectively and sequentially render, via a display, one or more of the plurality of correlated image pairs, the fusion images, and a third tomographic medical (TTM) image of the subject when an input signal is received from an I/O device, the TTM image depicts a second anatomical plane and is captured via a third MIT; and
  - selectively render, via the display, a visual representation of one or more of a pixel of interest and a region of interest for one or more of the plurality of correlated image pairs, the fusion images, and the TTM image when input is received from the I/O device, one or more of the pixel of interest and the region of interest is associated with a medical condition.

2. The system of claim 1, wherein one of the first MIT, the second MIT, and the third MIT comprises one of an X-ray, a computed tomography (CT) scan, a magnetic resonance imaging (MRI) scan, a positron emission tomography (PET) scan, and a maximum intensity projection (MIP) scan.

3. The system of claim 2, wherein the first MIT comprises the CT scan.

4. The system of claim 2, wherein the second MIT comprises the PET scan.

5. The system of claim 2, wherein the third MIT comprises the MIP scan.

6. The system of claim 2, wherein program instructions to selectively render one or more of each correlated image pair, the fusion image, and the TTM image further comprise program instructions to:

sequentially render one or more of each of the plurality of correlated image pairs and each fusion image when the input signal is received from the I/O device.

7. The system of claim 6, wherein
program instructions to selectively render the visual representation of the pixel of interest further comprise program instructions to:
- identify, using a machine learning algorithm, a pixel of one the first STM images or one of the second STM images that is associated with the medical condition, the pixel comprises a pixel location;
- render, via the display a graphical annotation at the pixel location; and
- the machine learning algorithm is trained with predetermined medical images that each depict a presence of the medical condition or absence of the medical condition within an anatomical region of the predetermined medical images, wherein the presence of the medical condition is dictated by a pixel value within the anatomical region that is greater than or less than a predetermined value.

8. The system of claim 7, wherein program instructions to selectively render the visual representation of the region of interest further comprise program instructions to:
- render, via the display, a second graphical annotation that encompasses the pixel location.

9. A computer-implemented method for synchronized navigation and annotation of correlated, heterogeneous sets of medical images, the method comprising:
- correlating, based on first metadata and second metadata, a first set of sequential tomographic medical (STM) images of a subject with a second set of STM images of the subject to generate a plurality of correlated image pairs, wherein the first set of STM images comprises the first metadata, and wherein the second set of STM images comprises the second metadata;
- superimposing each of the plurality of correlated image pairs to generate a plurality of fusion images each corresponding to one of the plurality of correlated image pairs;
- selectively and sequentially rendering, via a display, one or more of each of the plurality of correlated image pairs, each fusion image, and a third tomographic medical (TTM) image of the subject when an input signal is received from an I/O device;
- selectively rendering, via the display, a visual representation of one or more of a pixel of interest and a region of interest for one or more of the plurality of correlated image pairs, the fusion image, and the TTM image when input is received from the I/O device;
- wherein:
  - the first set of STM images each depict a first anatomical plane and are captured via a first medical imaging technique (MIT);
  - the second set of STM images each depict the first anatomical plane and are captured via a second MIT;
  - the TTM image depicts a second anatomical plane and is captured via a third MIT; and
  - one or more of the pixel of interest and the region of interest is associated with a medical condition.

10. The computer-implemented method of claim 9, wherein one of the first MIT, the second MIT, and the third MIT comprises one of an X-ray, a computed tomography (CT) scan, a magnetic resonance imaging (MRI) scan, a positron emission tomography (PET) scan, and a maximum intensity projection (MIP) scan.

11. The computer-implemented method of claim 10, wherein the first MIT comprises the CT scan.

12. The computer-implemented method of claim 11, wherein the second MIT comprises the PET scan.

13. The computer-implemented method of claim 12, wherein the third MIT comprises the MIP scan.

14. The computer-implemented method of claim 13, wherein the step of selectively rendering one or more of each of the plurality of correlated image pairs, the fusion image, and the TTM image further comprises:

sequentially rendering one or more of each of the plurality of correlated image pairs and the fusion image when the input signal is received from the I/O device.

15. The computer-implemented method of claim 14, wherein the step of selectively rendering the visual representation of the pixel of interest further comprises:

identifying, using a machine learning algorithm, a pixel of one the first STM images or one of the second STM images that is associated with the medical condition, the pixel comprising a pixel location;

rendering, via the display, a graphical annotation at the pixel location; and the machine learning algorithm is trained with predetermined medical images that each depict a presence of the medical condition or absence of the medical condition within an anatomical region of the predetermined medical images, wherein the presence of the medical condition is dictated by a pixel value within the anatomical region that is greater than or less than a predetermined value.

16. The computer-implemented method of claim 15, wherein the step of selectively rendering the visual representation of the region of interest further comprises:

rendering, via the display, a second graphical annotation that encompasses the pixel location.

17. A computer program product, the computer program product comprising a computer readable storage medium having program code embodied therewith, the program code executable by a processor to:

correlate, based on a first metadata and a second metadata, a first set of sequential tomographic medical (STM) images of a subject with a second set of STM images of the subject and thereby generate a plurality of correlated image pairs, superimpose each of the plurality of correlated image pairs to generate a plurality of fusion images each corresponding to one of the plurality of correlated image pairs;

selectively and sequentially render, via a display, one or more of the plurality of correlated image pairs, the fusion images, and a third tomographic medical (TTM) image of the subject when an input signal is received from an I/O device, the TTM image depicts a second anatomical plane and is captured via a third MIT;

selectively render, via the display, a visual representation of one or more of a pixel of interest and a region of interest for one or more of the plurality of correlated image pairs, the fusion images, and the TTM image when input is received from the I/O device;

wherein:

the first set of STM images each comprise the first metadata, depict a first anatomical plane and are captured via a first medical imaging technique (MIT);

the second set of STM images each comprise the second metadata, depict the first anatomical plane and are captured via a second MIT; and one or more of the pixel of interest and the region of interest is associated with a medical condition.

18. The computer program product of claim 17, wherein one of the first MIT, the second MIT, and the third MIT comprises one of an X-ray, a computed tomography (CT) scan, a magnetic resonance imaging (MRI) scan, a positron emission tomography (PET) scan, and a maximum intensity projection (MIP) scan.

19. The computer program product of claim 18, wherein the program code to selectively render the visual representation of the pixel of interest further comprises computer code executable by the processor to:

identify, using a machine learning algorithm, a pixel of one the first STM images or one of the second STM images that is associated with the medical condition, the pixel comprising a pixel location;

render, via the display, a graphical annotation at the pixel location; and the machine learning algorithm is trained with predetermined medical images that each depict a presence of the medical condition or absence of the medical condition within an anatomical region of the predetermined medical images, wherein the presence of the medical condition is dictated.

20. The computer program product of claim 19, wherein the program code to selectively render the visual representation of the region of interest further comprises program code executable by the processor to:

render, via the display, a second graphical annotation that encompasses the pixel location.

\* \* \* \* \*